United States Patent [19]

Richard et al.

[11] Patent Number: 5,755,769
[45] Date of Patent: May 26, 1998

[54] EXPANSIBLE ENDOPROSTHESIS FOR A HUMAN OR ANIMAL TUBULAR ORGAN, AND FITTING TOOL FOR USE THEREOF

[75] Inventors: Thierry Richard, Paris; Eric Perouse, L'Isle Adam, both of France

[73] Assignee: Laboratoire Perouse Implant, Bornel, France

[21] Appl. No.: 146,137

[22] PCT Filed: Mar. 11, 1993

[86] PCT No.: PCT/FR93/00246

§ 371 Date: Apr. 21, 1994

§ 102(e) Date: Apr. 21, 1994

[87] PCT Pub. No.: WO93/18317

PCT Pub. Date: Sep. 16, 1993

[30] Foreign Application Priority Data

Mar. 12, 1992 [FR] France ............... 92 02971

[51] Int. Cl.⁶ ............................................. A61F 2/06
[52] U.S. Cl. ............................................... 623/11
[58] Field of Search ....................... 623/1, 12, 900; 606/191–198

[56] References Cited

U.S. PATENT DOCUMENTS

| | | |
|---|---|---|
| 4,447,222 | 5/1984 | Sartinoranont. |
| 4,731,073 | 3/1988 | Robinson ............... 623/1 |
| 4,878,906 | 11/1989 | Lindemann et al. . |
| 4,955,859 | 9/1990 | Zilber . |
| 4,990,155 | 2/1991 | Wilkoff . |
| 5,047,050 | 9/1991 | Arpesani ............... 623/1 |
| 5,061,275 | 10/1991 | Wallsten et al. ............... 623/1 |
| 5,064,435 | 11/1991 | Porter ............... 623/12 |
| 5,116,318 | 5/1992 | Hillstead ............... 604/96 |
| 5,123,917 | 6/1992 | Lee ............... 623/1 |
| 5,211,658 | 5/1993 | Clouse ............... 623/1 |
| 5,356,425 | 10/1994 | Tihon et al. ............... 606/194 |

FOREIGN PATENT DOCUMENTS

| | | |
|---|---|---|
| 0 364 420 | 4/1990 | European Pat. Off. . |
| 364787 | 4/1990 | European Pat. Off. ............... 623/1 |
| 0 408 245 | 1/1991 | European Pat. Off. . |
| 0 423 916 | 4/1991 | European Pat. Off. . |
| 556850 | 8/1993 | European Pat. Off. ............... 623/1 |
| 621015 | 10/1994 | European Pat. Off. ............... 623/1 |
| 90 01 160.0 | 5/1990 | Germany . |
| 39 18 736 | 12/1990 | Germany . |
| 335341 | 10/1989 | Japan ............... 623/1 |
| 2 189 150 | 10/1987 | United Kingdom . |
| 24961 | 11/1994 | WIPO ............... 623/1 |

Primary Examiner—Michael J. Milano
Attorney, Agent, or Firm—Wenderoth, Lind & Ponack

[57] ABSTRACT

An endoprosthesis includes an extensible tubular mesh embedded in a plastic or elastomer extensible film. A tool for positioning the endoprosthesis includes a tube-shaped guide provided at its distal end with a tulip-shaped housing. Cutting threads cause the housing to open longitudinally into several petal-like parts. Application is to endoluminal treatment of aneurisms and dilations.

30 Claims, 3 Drawing Sheets

1

EXPANSIBLE ENDOPROSTHESIS FOR A HUMAN OR ANIMAL TUBULAR ORGAN, AND FITTING TOOL FOR USE THEREOF

BACKGROUND OF THE INVENTION

The present invention relates to an expansible endoprosthesis for a human or animal tubular organ, of the type comprising an expansible mesh of cylindrical general shape, and is useful in particular for the endoluminal treatment of aneurisms and to dilations.

Endoprostheses of this type generally consist of a single metal mesh which can be expanded using a balloon, or are auto-expansible, i.e. self-expanding. After a transluminal dilation, they are inserted endoluminally using a probe, then expanded or released.

These known endoprostheses are not entirely satisfactory, because the tissues penetrate the cavities of the mesh and are traumatized and, in addition, the endoprosthesis creates turbulence in the blood flow.

Furthermore, these endoprostheses cannot be used for treating aneurisms, or more generally for connecting two healthy segments of a tubular organ such as a vessel, since they are not liquid-tight.

SUMMARY OF THE INVENTION

The object of the invention is to provide an expansible endoprosthesis which eliminates these draw-backs. For this purpose, the invention provides an endoprosthesis of the aforementioned type, but wherein a mesh is embedded in an extensible and biocompatible plastic or elastomer film, this film filling the cavities of the mesh and covering the entire surface of the mesh substantially throughout the whole extent of the endoprosthesis.

According to other characteristics:

the film consists of a polymer such as polyurethane or a natural or synthetic rubber;

the endoprosthesis is of the auto-expansible or self-expanding type, and the end parts of the endoprosthesis are flared when it is in its expanded state;

the mesh is made of stainless steel or of a relatively rigid plastic such as polytetrafluoroethylene which has been made radiopaque.

Another aspect of the invention is a tool for fitting an auto-expansible endoprosthesis as defined above. This tool comprises:

a guide tube provided at its distal end with a tulip-shaped part for housing the endoprosthesis in the contracted state; and means for opening the tulip-shaped part longitudinally.

According to one embodiment, such means comprise wires for cutting the tulip-shaped part into several petal-like parts, such wires being connected to an actuation handle.

According to another embodiment, such means comprise a longitudinal opening of the tulip-shaped part, each edge of which has a series of gussets, the gussets of the two edges being fitted into each other and being held by a cord which passes through them and which is connected to an actuation handle.

BRIEF DESCRIPTION OF THE DRAWINGS

Embodiments of the invention will now be described with reference to the attached drawings, in which.

DETAILED DESCRIPTION OF THE INVENTION

Figure 1:
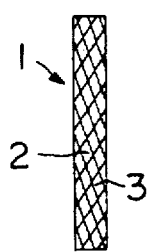
FIG. 1 diagrammatically represents an endoprosthesis according to the invention in a retracted state.
Figure 2:
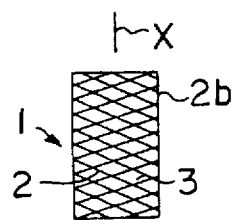
FIG. 2 diagrammatically represents the same endoprosthesis in an expanded state.

The endoprosthesis 1 represented in FIGS. 1 and 2 consists of a tubular mesh 2 embedded in a film 3.

The mesh consists of stainless steel of biocompatible grade. Mesh 2 can be made by weaving or knitting of a yarn, axial spreading of a tube, or by any other suitable technique. It is plastically deformable, that is to say that it has a first stable shape of small diameter, represented in FIG. 1, in which the cavities form diamonds elongated parallel to its axis, and a second stable shape of greatly enlarged diameter and shorter length, represented in FIG. 2, in which the cavities form diamonds elongated in the circumferential direction. Mesh 2 has an axis X (FIG. 2), opposite ends or end portions and a body or main portion extending between said end portions, as clearly illustrated. The material of mesh 2 has an exposed surface including (with reference to FIG. 7A for purposes of clarity of illustration) portions 2a facing radially inwardly with respect to axis X, portions 2b facing radially outwardly with respect to axis X, and portions 2c facing toward and defining each of the cavities.

The mesh 2 is entirely embedded in film 3 of an extensible and liquid-tight material which fills its cavities. Film 3 covers and is attached to the entire exposed surface of mesh 2 including portions 2a thereof defining the cavities therein. The extensibility of this material is sufficient for the film 3 to be able to follow the deformation of the mesh 2 from its contracted state to its expanded state without tearing or detachment, despite the deformation of the cavities of the mesh. Appropriate materials are a biocompatible elastomer, which may be a natural or synthetic rubber, or alternatively a biocompatible polymer such as polyurethane.

The coating of the mesh 2 with the film 3 may be carried out by techniques of co-extrusion or immersion, after degreasing of the metal and its treatment with a primary adhesion substance.

In the expanded state (FIG. 2), a liquid-tight tubular segment is then obtained which can be used as an endoprosthesis or "stent" after a transluminal dilation. This endoprosthesis does not traumatize the tissues and creates practically no turbulence in the blood flow, since the tissues and the blood are in contact with a practically smooth elastomer or polymer surface.

Because of its leaktightness, the endoprosthesis can be used for endoluminal treatment of an aneurism, by making it bridge the aneurism, each of its ends being applied radially against the inner wall of a healthy artery segment adjacent to the aneurism.

In another embodiment, illustrated in FIGS. 3 to 7, the mesh 2 of the endoprosthesis 1A is auto-expansible, which is obtained conventionally by using stainless steel with spring properties.

Figure 3:
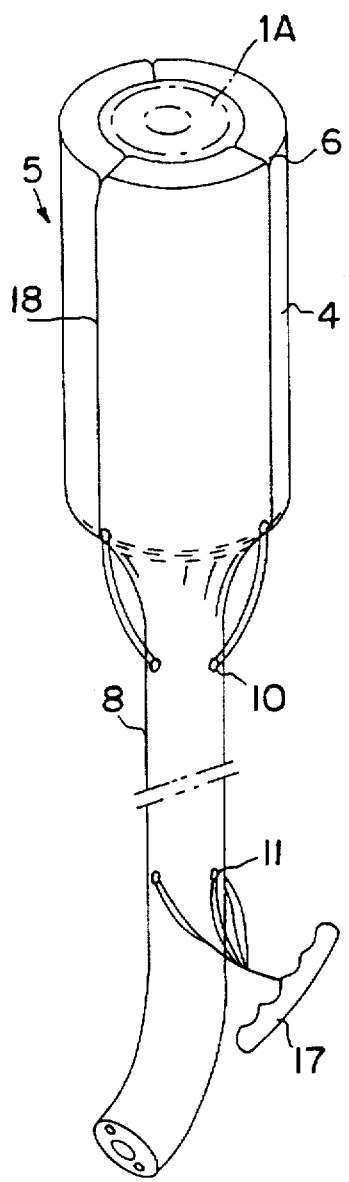
FIG. 3 represents, on a greatly enlarged scale, in perspective, a tool for fitting an auto-expansible endoprosthesis according to the invention.
Figure 4:
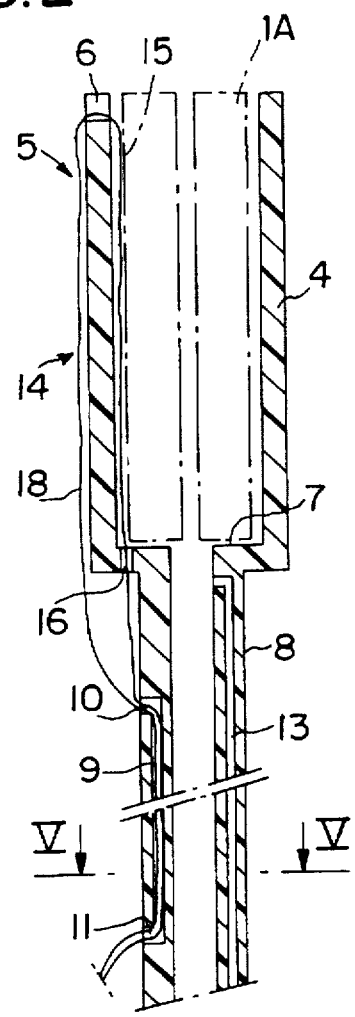
FIG. 4 is a view in longitudinal section of the tool in FIG. 3.
Figure 5:
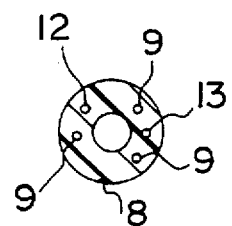
FIG. 5 is a view taken in section along the line V—V in FIG. 4.

For fitting the endoprosthesis 1A, it is compressed radially into its configuration in FIG. 1, which is not stable, and it is inserted into a tulip-shaped end 4 of a tool 5 represented in FIGS. 3 to 5.

The distal end of the tulip-shaped part 4 is open and has three notches 6 spaced at angles of 120° from each other. Its proximal end forms an inner shoulder 7 from which extends a guide tube 8. In the plane of each notch 6, a channel 9 formed in the thickness of the wall of the tube 8 emerges outwards through radial orifices 10, 11, on the one hand near the shoulder 7, and on the other hand near the proximal end of the tube 8.

It is also possible to provide in the thickness of the wall of the tube 8, as shown, longitudinal channels 12, 13 for injecting fluids, which channels start from the proximal end of tube 8 and emerge into a space inwardly of the tube 8 near the shoulder 7.

In each of the three aforementioned planes, a flexible wire 14 passes through the respective notch 6. An inner strand 15 of wire 14 runs along the inner wall of the tulip-shaped part 4, passes through an orifice 16 provided in the shoulder 7, penetrates the orifice 10, extends along the channel 9, leaves through the orifice 11 and rejoins an actuation handle 17 (FIG. 3). An outer strand 18 of the wire 14 runs along the outer wall of the tulip-shaped part, follows the same path 10, 9, 11 as the strand 15, and also rejoins the handle 17. Handle 17 is therefore connected to six wire strands, and the three inner strands 15 are pressed flat against the inner wall of the tulip-shaped part by the tendency of the endoprosthesis 1A to expand.

Before using the endoprosthesis, after a transluminal dilation or for treating an aneurism, the tool 5 is threaded onto a guide, inserted through the skin and conveyed endoluminally as far as the desired location.

Figures 6, 7, 7A:
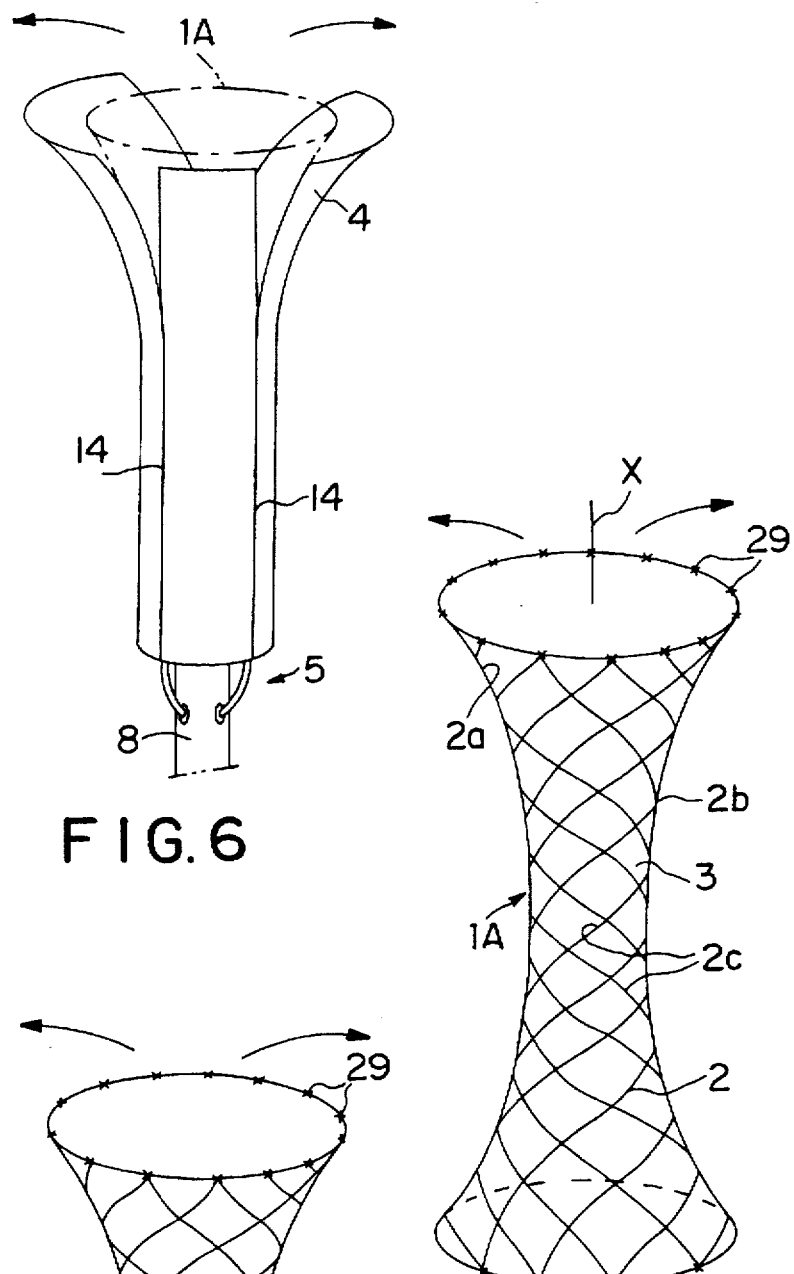
FIG. 6 illustrates the use of the tool in FIGS. 3 to 5.
FIG. 7 represents the corresponding expansion of the endoprosthesis.
FIG. 7A shows flaring of end portions.

The operator then pulls on the handle 17. This tensions the three wires 15, and these wires each cut the tulip-shaped part 4 along one generatrix. The tulip-shaped part then progressively releases the endoprosthesis, which expands by itself, as illustrated in FIG. 6. When the tulip-shaped part is completely open, the tool is withdrawn by pulling on the tube 8.

In the expanded state (FIG. 7A), it is seen that the two ends of the endoprosthesis are automatically flared, which provides two advantageous effects: on the one hand, the leaktightness of the endoprosthesis and the artery is reinforced, and, on the other hand, the ends 29 of the wires of the mesh 2 extend slightly beyond the film 3 and form as many points for anchoring the endoprosthesis in the artery. The endoprosthesis is thus positionally stabilized.

Other materials may be used to form the mesh 2. For example, in order to produce an auto-expansible endoprosthesis, a yarn of a relatively rigid polymer with spring properties, such as polytetrafluoroethylene (PTFE), which has been made radiopaque, may be used.

Figure 8:
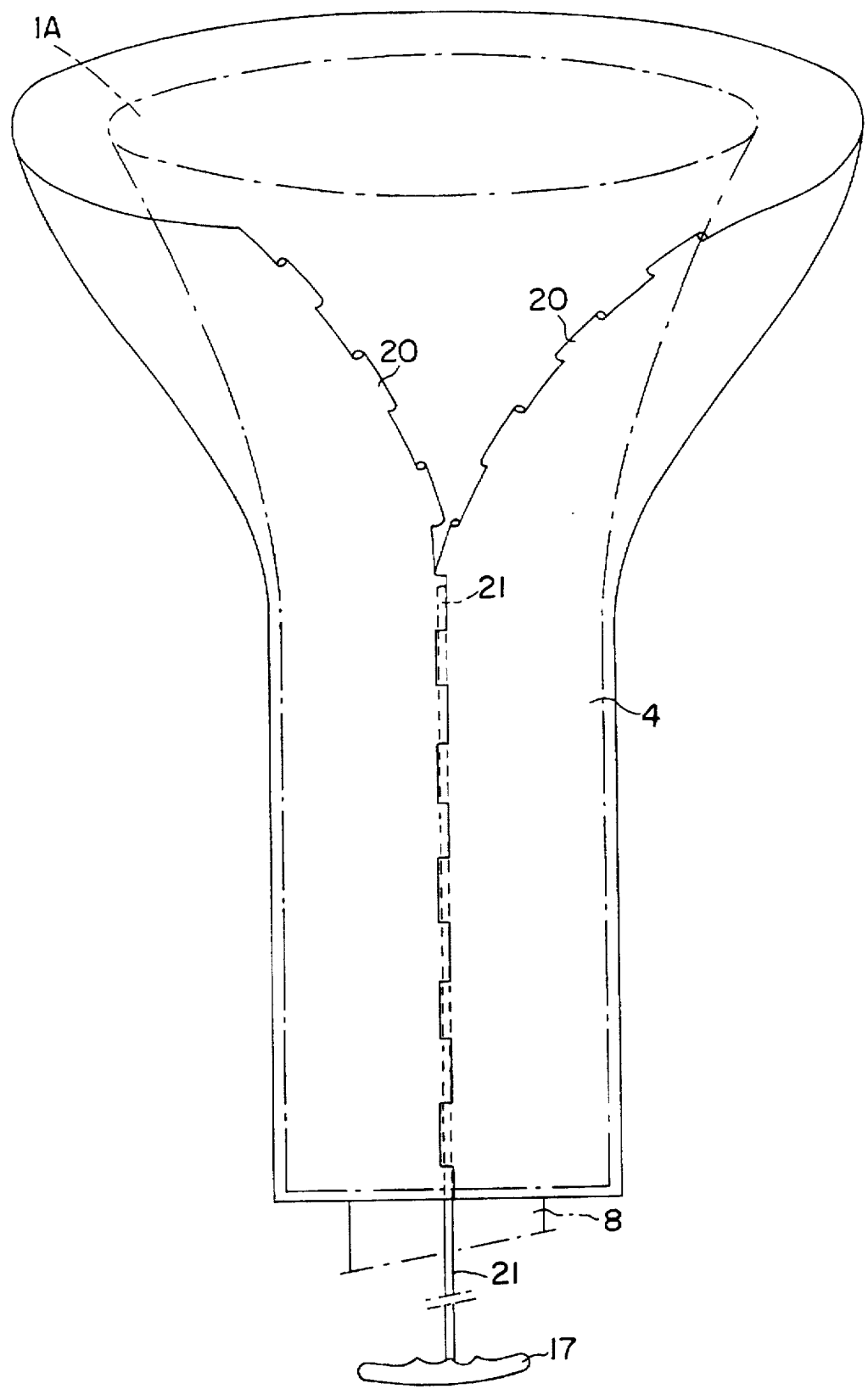
FIG. 8 diagrammatically represents, on a greatly enlarged scale and in perspective, another tool for fitting an auto-expansible endoprosthesis according to the invention.

Another embodiment of the tool 5 has been represented diagrammatically in FIG. 8. This tool differs from that described hereinabove by the means for longitudinal opening of the tulip-shaped part.

The tulip-shaped part is actually slit longitudinally over its entire height. Each edge of the slot includes a series of projecting cylindrical gussets 20. When the tulip-shaped part is in its closed cylindrical state, and holds an auto-expansible endoprosthesis 1A in the contracted state, the gussets 20 of the two edges interpenetrate, and the whole is held by a cord 21 which passes through all the gussets and is connected, at its proximal end, to the actuation handle 17.

The endoprosthesis is released simply by pulling on the handle 17.

We claim:

1. A self-expanding stent comprising:
   a generally tubular self-expanding mesh formed of a material having spring properties, said mesh having an axis, opposite ends and a body portion extending axially between said ends, said mesh defining therethrough a plurality of openings, and said material of said mesh having an exposed surface including portions facing radially outwardly and radially inwardly with respect to said axis and portions facing toward each of said openings, said mesh being deformably expansible from a contracted state to an expanded state;
   a liquid-tight film formed of an extensible and biocompatible material;
   at least said body portion of said mesh being entirely embedded within said film, such that said film fills and bridges said openings of said body portion of said mesh, and with said film covering and being attached to the entire said exposed surface of said body portion of said mesh; and
   said material of said film having an extensibility sufficient to enable said film to follow and move with said mesh during deformation thereof from said contracted state to said expanded state.

2. A stent as claimed in claim 1, wherein said film material is a polymer.

3. A stent as claimed in claim 1, wherein said film material is polyurethane.

4. A stent as claimed in claim 1, wherein said film material is natural rubber.

5. A stent as claimed in claim 1, wherein said film material is synthetic rubber.

6. A stent as claimed in claim 1, wherein end portions of said stent are flared when said stent is in an expanded condition thereof.

7. A stent as claimed in claim 1, wherein said mesh material comprises stainless steel.

8. A stent as claimed in claim 1, wherein said mesh material comprises a rigid plastic.

9. A stent as claimed in claim 8, wherein said rigid plastic mesh material comprises polytetrafluoroethylene.

10. A stent as claimed in claim 8, wherein said rigid plastic mesh material is radiopaque.

11. A stent as claimed in claim 1, wherein said film is a plastic material.

12. A stent as claimed in claim 1, wherein said film is an elastomer material.

13. A stent as claimed in claim 1, wherein said openings of said mesh are diamond-shaped and are elongated parallel to said axis of said mesh in said contracted state of said mesh and are elongated circumferentially of said mesh in said expanded state of said mesh.

14. A stent as claimed in claim 1, wherein said extensibility of said material of said film is sufficient to prevent said film from tearing away or detaching from said mesh during said deformation.

15. A stent as claimed in claim 1, wherein said film comprises a unitary one-piece structure.

16. An expansible stent comprising:

a generally tubular mesh having an axis, opposite ends and a body portion extending axially between said ends, said mesh defining therethrough a plurality of openings, and said mesh having an exposed surface including portions facing radially outwardly and radially inwardly with respect to said axis and portions facing toward each of said openings, said mesh being deformably expansible from a contracted state to an expanded state;

a liquid-tight film formed of an extensible and biocompatible material;

at least said body portion of said mesh being entirely embedded within said film, such that said film fills and bridges said openings of said body portion of said mesh, and with said film covering and being attached to the entire said exposed surface of said body portion of said mesh; and said material of said film having an extensibility sufficient to enable said film to follow and move with said mesh during deformation thereof from said contracted state to said expanded state.

17. A stent as claimed in claim 16, wherein said film material is a polymer.

18. A stent as claimed in claim 16, wherein said film material is polyurethane.

19. A stent as claimed in claim 16, wherein said film material is natural rubber.

20. A stent as claimed in claim 16, wherein said film material is synthetic rubber.

21. A stent as claimed in claim 16, wherein end portions of said stent are flared when said stent is in an expanded condition thereof.

22. A stent as claimed in claim 16, wherein said mesh is formed of stainless steel.

23. A stent as claimed in claim 16, wherein said mesh is formed of a rigid plastic.

24. A stent as claimed in claim 23, wherein said rigid plastic comprises polytetrafluoroethylene.

25. A stent as claimed in claim 23, wherein said rigid plastic is radiopaque.

26. A stent as claimed in claim 16, wherein said film is a plastic material.

27. A stent as claimed in claim 16, wherein said film is an elastomer material.

28. A stent as claimed in claim 16, wherein said openings of said mesh are diamond-shaped and are elongated parallel to said axis of said mesh in said contracted state of said mesh and are elongated circumferentially of said mesh in said expanded state of said mesh.

29. A stent as claimed in claim 16, wherein said extensibility of said material of said film is sufficient to prevent said film from tearing away or detaching from said mesh during said deformation.

30. A stent as claimed in claim 16, wherein said film comprises a unitary one-piece structure.

* * * * *